(12) United States Patent
Kinnunen

(10) Patent No.: US 8,690,424 B2
(45) Date of Patent: Apr. 8, 2014

(54) PATIENT STOOL FOR AN X-RAY IMAGING APPARATUS

(75) Inventor: Jouni Kinnunen, Helsinki (FI)

(73) Assignee: Planmed Oy, Helsinki (FI)

( * ) Notice: Subject to any disclaimer, the term of this patent is extended or adjusted under 35 U.S.C. 154(b) by 0 days.

(21) Appl. No.: 13/695,068

(22) PCT Filed: Apr. 28, 2011

(86) PCT No.: PCT/FI2011/050390
§ 371 (c)(1),
(2), (4) Date: Oct. 29, 2012

(87) PCT Pub. No.: WO2011/135189
PCT Pub. Date: Nov. 3, 2011

(65) Prior Publication Data
US 2013/0044857 A1 Feb. 21, 2013

(30) Foreign Application Priority Data

Apr. 29, 2010 (FI) .................................... 20100180
Apr. 29, 2010 (FI) .................................... 20100181
Nov. 25, 2010 (FI) .................................... 20100395

(51) Int. Cl.
*H05G 1/02* (2006.01)
*H05G 1/00* (2006.01)

(52) U.S. Cl.
USPC .............. 378/196; 378/20; 378/195; 378/208

(58) Field of Classification Search
USPC ........ 378/4–20, 193–198, 204, 208, 210, 205
See application file for complete search history.

(56) References Cited

U.S. PATENT DOCUMENTS

| | | |
|---|---|---|
| 5,042,487 A | 8/1991 | Marquardt |
| 5,574,763 A | 11/1996 | Dehner |
| 5,899,859 A | 5/1999 | Votruba et al. |
| 6,315,445 B1 * | 11/2001 | Mazess et al. ................ 378/196 |
| 7,108,421 B2 | 9/2006 | Gregerson et al. |
| 7,388,941 B2 | 6/2008 | Sukovic et al. |
| 2004/0022350 A1 * | 2/2004 | Gregerson et al. ............ 378/15 |
| 2006/0245539 A1 * | 11/2006 | Sukovic et al. ................ 378/20 |
| 2009/0003532 A1 | 1/2009 | Weber |
| 2009/0289633 A1 | 11/2009 | Dutto et al. |
| 2010/0078481 A1 | 4/2010 | Trajkovic |

FOREIGN PATENT DOCUMENTS

WO 02094100 A1 11/2002
WO WO2010/078481 7/2010

* cited by examiner

*Primary Examiner* — Anastasia Midkiff
(74) *Attorney, Agent, or Firm* — Fay Sharpe LLP

(57) ABSTRACT

The invention relates to a medical x-ray imaging apparatus including a support structure (1) which supports a substantially ring-shaped structure, an O-arm (2) supporting imaging means (21, 22), to which O-arm (2) is arranged an examination opening (4). The ring-shaped structure (2) supporting the imaging means is arranged movable with respect to said support construction (1) at least in vertical direction. A patient stool (30) is arranged to be positioned in connection with the apparatus, as well as positioning means (32, 33, 34) in connection with said examination opening (4) for positioning the patient stool (30) in the examination opening (4).

15 Claims, 4 Drawing Sheets

PATIENT STOOL FOR AN X-RAY IMAGING APPARATUS

FIELD OF INVENTION

The invention relates to a patient stool arrangement used in connection with a medical x-ray imaging apparatus according to the preamble of claim 1.

BACKGROUND OF INVENTION

Conventional apparatuses employed in medical x-ray imaging most simple of their basic structure comprise a source of radiation which is used together with a film cassette separate from the source of radiation. Hospitals commonly use also the so-called C-arch x-ray apparatuses where the source of radiation and the receiver of image information are arranged at the opposite ends of the arched arm part. Conventionally, a device group of its own consists of large-size and extremely expensive computed tomography apparatuses where the patient is typically positioned for imaging in the recumbent position within a ring-shaped or tubular structure.

Computed tomography apparatuses have also been developed into more lightweight versions. As an example of prior art arrangements, we refer to U.S. Pat. Nos. 7,108,421 and 7,388,941. In such apparatuses, imaging means rotatable for 360 degrees around the imaging station are arranged within a ring-shaped O-arm supported from the side. The O-arm may be arranged adjustable for its height position and turnable with respect to a horizontal axis.

As conventional computed tomography apparatuses have been quite massive and expensive, acquiring them e.g. for the use of hospital emergency rooms has not been possible in practice. On the other hand, it is also typical for commercial computed tomography apparatuses that they are not necessarily designed for imaging some specific anatomy or anatomies but they are more or less general imaging apparatuses. If e.g. desiring to image the patient's whole torso, the imaging station to be arranged to the apparatus as well as other dimensions of the apparatus have had to be implemented in respective proportions.

BRIEF DESCRIPTION OF INVENTION

The object of the present invention is to advance the state of the art concerning x-ray imaging apparatuses less expensive and of smaller size as compared to the conventional computed tomography apparatuses. The embodiments of the invention preferably offer a possibility to implement a cone-beam computed tomography imaging apparatus particularly designed applicable for imaging extremities, for example, the properties and price of which could bring purchase of the apparatus within resources available for e.g. emergency clinics. As the conventional computed tomography employs a narrow fan-like beam, in cone-beam tomography the beam is collimated to be genuinely two-dimensional but often to cover only a quite small specific area (volume) of the object being imaged. A special object of the invention is to advance development particularly in the field of x-ray imaging apparatuses comprising a ring-shaped arm part of the above-described type.

Especially, the object of the invention relates to facilitating realization of such special imaging mode, in which the patient's leg is imaged in a standing position. This type of so-called weight-bearing imaging may under certain circumstances give more information, or more relevant information, for diagnosis than imaging an extremity in "a rest state".

Essential characteristics of the invention are described in the accompanying patent claims. Especially essential for the invention and for preferable embodiments of the invention is a stool arrangement adapted to be fitted in connection with an examination opening of the imaging device. The stool arrangement facilitates placing oneself for imaging, on one hand, and makes it easier to image lower parts of a leg, an ankle etc. also in standing position, on the other. Below, the invention and some of its preferable embodiments are described in more detail and by also referring to the attached figures.

DETAILED DESCRIPTION OF INVENTION

In the following, the terms centre and central axis will be used in connection with structures which do not necessarily form a true, full circle but are of circular shape only for their prevailing part. To avoid ambiguity, these terms refer in connection with this specification to a point and an axis which would be the centre or central axis of the structure in question in case that structure would form a full or a pure circle.

Furthermore, concerning one component of the apparatus according to the invention, this specification employs terms a substantially ring-shaped structure and an O-arm. When the dimension in the direction of the central axis of this structure can be significantly large with respect to the diameter of the ring-shaped structure in question, for the avoidance of doubt it is stated that in the following, vertical position of the O-arm refers to a position where the central axis of the O-arm is horizontally oriented and horizontal position of the O-arm refers to a position where its central axis is vertically oriented.

Figure 1:
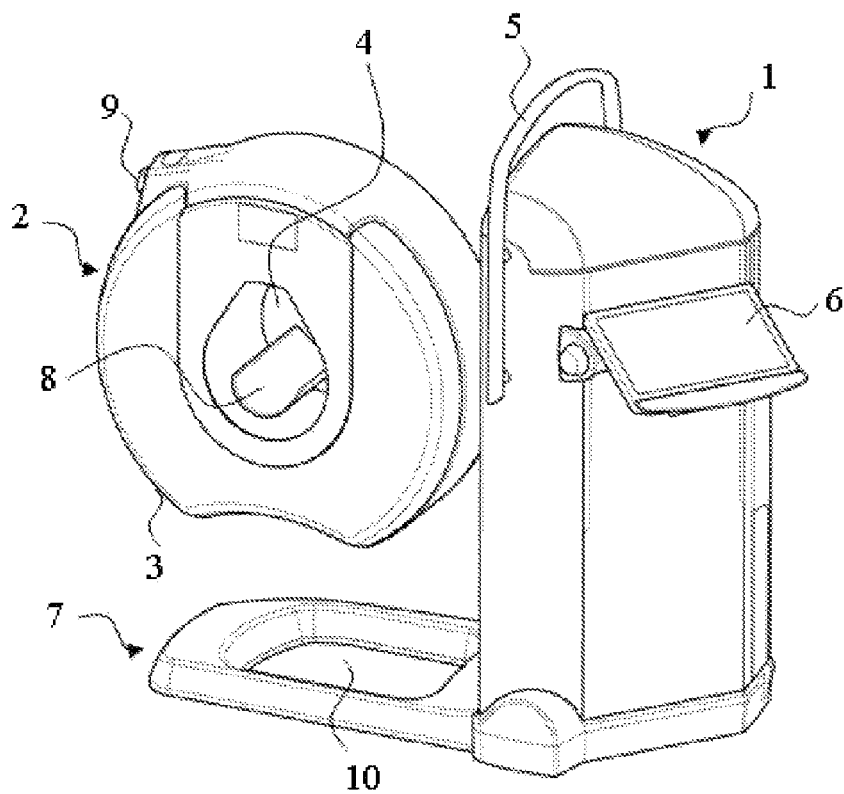
FIG. 1 shows a general view of an x-ray imaging apparatus, its basic structure including a support construction and a substantially ring-shaped O-arm.

FIG. 1 shows a general view of one imaging apparatus according to the invention. The basic structure of the apparatus includes a support construction (1) which supports a substantially ring-shaped structure (2) within which imaging means (21, 22) of the apparatus are located and which is also referred to as an O-arm in this context. This O-arm (2) is arranged with an examination opening (4) within which an anatomy to be imaged is positioned. FIG. 1 further shows a patient support rail (5) arranged to the support construction (1), a user interface (6) being in functional connection with a control system of the apparatus, a possibly detachably attached pedestal or base part (7) projecting substantially in the direction of the O-arm, and a positioning support (8) arranged to the examination opening (4).

Mounting of the structure (2) supporting the imaging means to the support construction (1) can be arranged to enable moving of the O-arm (2), such as adjustment of its height position. The O-arm (2) can also be arranged to be turnable in at least one direction for at least 90 degrees from the vertical position shown in FIG. 1) to the horizontal position and, on the other hand, movable also in horizontal direction. These movements may be realized with the help of one or more actuator (M) and control of these manoeuvres can be arranged implementable aside from the user interface (6) also by means of a joy stick (9) arranged into connection with the O-arm (2) and/or the support frame (1).

When looking at the cross-section perpendicular to the direction of the central axis of the O-arm (2) shown in FIG. 1, i.e. the radial cross-section of the O-arm (2), an outer cover (3) of the O-arm (2) forms for its prevailing part a circle which yet comprises a sector where the distance from the centre of said circle to the edges of the outer cover (3) is smaller than the radius of that portion being circular for its prevailing part. In the embodiment of the invention according to FIG. 1, the part in said sector being cut off the O-arm (2) is evenly curved in the opposite direction with respect to the arch of the circle of the prevailing portion of the outer cover (3), but this cut part can also be of some other shape, such as wedge-shaped, rectangular, straight or even curved in the same direction as the portion of the arch of the outer cover (3) substantially of the shape of a circle.

When a sector of the kind described above is arranged at a section of the O-arm (2) substantially orienting downwards or being orientable downwards, it can be easier to implement e.g. imaging of lower extremities in sitting position when thanks to the invention, the examination opening (4) can be driven closer to the floor level as compared to an O-arm (2) not comprising such a cut. On the other hand, if the imaging apparatus is provided with a possibility to adjust the height position of the O-arm (2) and to turn the O-arm (2) to a position where the central axis of the O-arm (2) is substantially vertical, one may use the apparatus to image the patient in a standing position, too. Then, said cut arranged to the O-arm (2) makes it easier for the patient to step into the examination opening (4) and out of the examination opening as the length of the step one needs to take over the 'doorstep' formed by the O-arm (2) will be shorter.

In the embodiment of the invention according to FIG. 1, the examination opening (4) is implemented only for its prevailing part substantially as a circle. A sector has been arranged to the examination opening (4) which forms an extension to the circle. That is, the examination opening (4) is provided with a sector in the area of which the distance of the edge of the examination opening (4) from the centre of the circular portion of the examination opening (4) (or from the central axis of the O-arm (2)) is longer than the radius of the circular portion of the examination opening (4). Such design of the examination opening (4) is preferable e.g. when the aim is to realize dimensions of the cross-section perpendicular with respect to the central axis of the O-arm structure as small as possible, such as when considering an embodiment basically designed for imaging anatomies having a smaller diameter than the diameter of the human torso, such as extremities.

Enlarging the examination opening (4) in some sector of the circle facilitates patient positioning e.g. when imaging a plastered leg. In such an embodiment of the invention we are talking about an examination opening (4) the diameter of the portion of the shape of an arch of a circle of which is e.g. of the order of 30-35 cm. In the preferable embodiment of the invention according to FIG. 1, the examination opening (4) is substantially of the shape of a droplet, i.e. the shape of its extension is substantially an equilateral triangle having a truncated apex, but said extension can naturally be of some other shape as well.

The above-described shapes of the outer cover (3) of the O-arm (2) differing from the circular shape are part of one preferable embodiment of the invention, but the outer cover (3) can also be implemented in some other shape.

Figure 2:
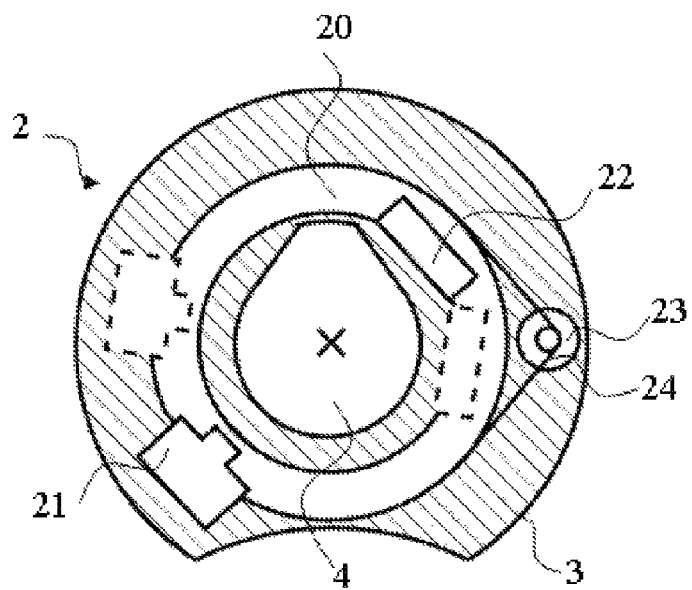
FIG. 2 shows one arrangement applicable for use in connection with the invention for arranging imaging means to the ring-shaped O-arm.

According to the basic structure of the apparatus, the imaging means, i.e. a source of radiation (21) and a receiver of image information (22), are arranged within the substantially ring-shaped structure (2) supporting the imaging means and as movable along a curved path within said structure, substantially on opposite sides of the examination opening (4). In FIG. 2, inside the O-arm (2) is arranged a ring-shaped support part (20) whereto substantially on opposite sides from each other are arranged the source of radiation (21) and the receiver of image information (22). The support part (20) is arranged rotatable within the structure (2) supporting the imaging means by means of an actuator (23) and a transmission belt (24). Hence, it is possible to image the object positioned at the examination opening (4) from different directions within the range of the angle of rotation of the imaging means and to create of thus acquired image information a voxel model by means of image-data processing methods known as such.

In the embodiment according to FIG. 2, the source of radiation (21) and the receiver of image information (22) are arranged movable within said substantially ring-shaped structure (2) supporting the imaging means with respect to a centre of rotation such that the source of radiation (21) (the focus of the source of radiation) moves at a different distance from said centre of rotation than the receiver of image information (22). In the arrangement according to FIG. 2, the source of radiation (21) is attached on the outer circumference of the ring-shaped support part (20) whereby, when rotating the support part (20), the focus of the source of radiation (21) moves farther from said centre of rotation than the receiver of image information (22) attached on the side of the inner circumference of the support part (20). When the receiver of image information (22) is thus brought closer to the volume being imaged, it is possible when using a detector (22) of given size to use a wider beam and thus increase the volume being imageable as compared to that the receiver of image information (22) were to move farther from the object.

The range of movement for the imaging means may also be implemented in another way than in some prior-art apparatuses of similar type, i.e. by arranging the source of radiation (21) and the receiver of image information (22) movable along a curved path substantially on opposite sides of the examination opening (4) for a shorter distance than 360 degrees. This distance is referred to in the context of this specification as an angle of rotation, and preferably it is arranged to be somewhat larger than 180 degrees but then substantially smaller than 360 degrees, such as of the order of 210+/−20 degrees. Then, arranging the imaging means (21, 22) to be movable at different distances from the centre of rotation may preferably be implemented particularly in an arrangement comprising the above-described cut in the O-arm (2) and extension in the examination opening (4). The range of manoeuvring of the source of radiation (21) can be arranged not to extend to that sector of the O-arm in which the outer cover (3) has been cut like described above and, on the other hand, the range of manoeuvring of the receiver of image information (22) not to extend to that sector of the O-arm (2) in which is arranged an extension of the examination opening (4) as described above. When the utmost dimensions of said extension and cut from the centre of rotation of the imaging means are arranged appropriate with respect to those different distances at which the imaging means are rotated from the centre of rotation, the apparatus can be implemented as shown in FIG. 3 such that the source of radiation (21) arranged to move farther from the centre of rotation is able to move outside the extension of the examination opening (4)

and the receiver of image information (22), again, inside the cut arranged to the outer cover (3) of the O-arm (2).

Especially, such embodiment of the invention enables a structure where, e.g. considering imaging of extremities, due to the extension arranged to the examination opening (4) it is possible to implement the diameter of the circular portion of the examination opening (4) smaller than would be possible without the extension sector and, further, it is possible to arrange the cut to the outer cover (3) of the O-arm (2) which facilitates several positioning procedures of a patient. Such an embodiment of the invention is implementable as a compact structure and it enables realizing both the examination opening (4) and the outer dimensions of the whole O-arm (2) smaller than would otherwise be possible.

It was mentioned above that the extension arranged to the examination opening (4) facilitates e.g. positioning of a plastered leg to the examination opening. Placing the anatomy to be imaged to the examination opening (4) can be further facilitated by arranging the patient positioning support (8) arranged in connection with the examination opening (4) movable or detachably attached such that it is both positionable to a desired location within the examination opening (4) for imaging and positionable or transferrable to a place where it impedes patient positioning as little as possible. The purpose of such patient positioning support (8) is to assist positioning of the anatomy being imaged to a desired point with respect to the O-arm (2). Preferably one patient positioning support (8) according to the invention comprises a concave structure whereto an upper or a lower extremity can be positioned for the duration of the imaging. By arranging the patient positioning support (8) detachably connectable, different positioning supports (8) can be connected to the apparatus for enabling use of the positioning support by taking into consideration the specific characteristics of a given imaging.

Figure 3A:
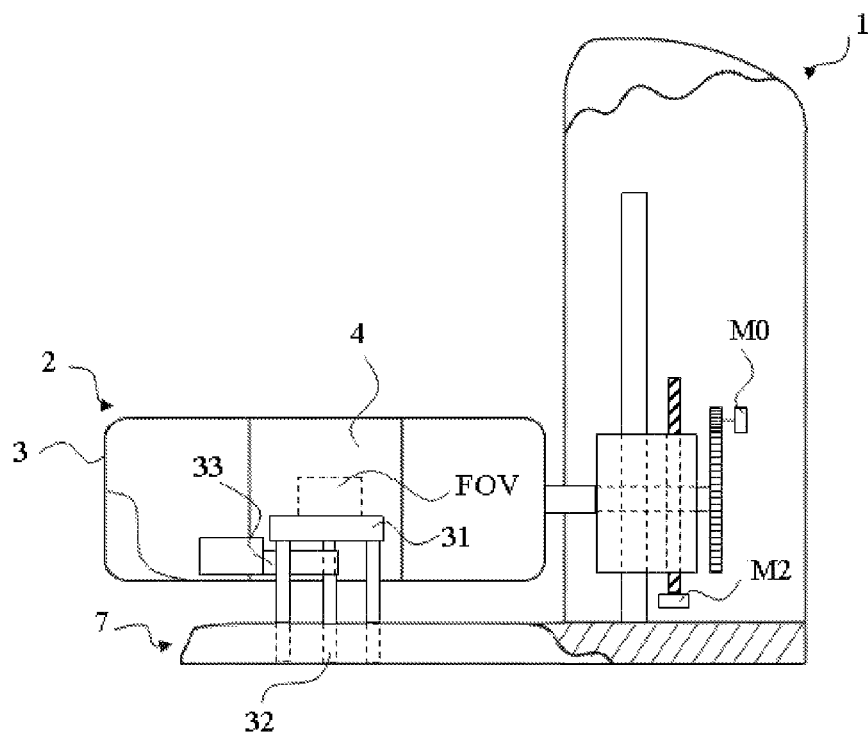
FIGS. 3a and 3b show one solution according to the invention for arranging a patient stool in connection with an imaging apparatus.
Figure 3B:
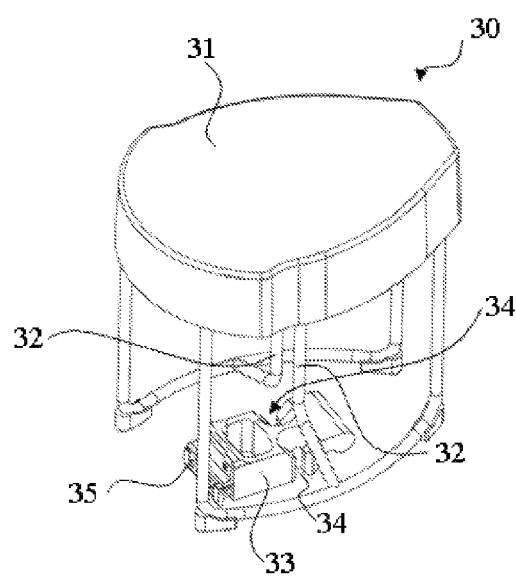

FIGS. 3a and 3b show one solution according to the invention for arranging a patient stool (30) in connection with the examination opening (4). Out of these, FIG. 3a shows an arrangement in principle for positioning the patient stool (30) in connection with the imaging opening (4), i.e. within the examination opening (4), when the O-arm (2) has been turned in a horizontal position, and FIG. 3b shows certain parts of the arrangement as detached from one another. In this embodiment of the invention, a guiding slide (33) attached to the O-arm (2) is arranged in connection with the examination opening (4). Two partially open holes or guiding grooves (34) are arranged to the guiding slide (33) and they have been such dimensioned that two guide-rods (32) arranged to the patient stool (30), which serve as legs for the stool as well, are able to move in the guiding grooves (33). The guiding rods (32) are such designed that they easily find their way and position themselves into their grooves (34), when one is placing the patient stool (30) to the examination opening (2) from above. The guiding slide (33) can be arranged to the O-arm (2) as a fixed construction or to be detachably connectable with the help of connecting means (35). In both cases, however, the guiding slide (33) or a corresponding structure and the guiding rods (32) or corresponding structures of the patient stool are preferably realized to form at least two support points such that the patient stool (30) always gets positioned accurately, steadily and non-rotatably at a desired place within the examination opening (4).

According to one preferable embodiment of the invention, the guiding slide (33) includes a means for connecting it detachably. Such means can be realized as a structure corresponding to the corresponding means of the abovementioned concave positioning support (8), whereby both of them can be connected to the same connecting structure arranged in connection with the O-arm (2).

In connection with the connecting arrangement of the patient stool (30), such as in connection with the connecting means (35) and the O-arm (2), for example, a means can be arranged to recognize a patient stool (30) being connected to the apparatus. Based on this identification, or by some other means, the control system of the apparatus can be arranged to set itself in an operation mode which, in view of patient safety, prevents potentially dangerous movements of the O-arm (2) as long as the stool (30) is connected to the O-arm (2). Such movements may include e.g. turning the O-arm (2) as well as driving the O-arm (2) in vertical direction beyond such operation range within which the stool (30) will stand on the floor. Preferably the connection mechanism of the stool (30) and/or the above-mentioned operation range are also realized such that it will not be possible to drive the O-arm (2) so low that the lower edge of its cover would locate on a lower level than the stepping-board (31) of the patient stool (30). By this arrangement a possibility is prevented, for example, that the patient stands on the stool (30) with toes outside thereof and when the O-arm (2) is driven downwards, the toes will be left between the stool (30) and the cover (3) of the O-arm.

The arrangement for positioning the patient stool (30) in the examination opening (4) can naturally also be different than presented in FIGS. 3a and 3b. Anyhow, preferably the arrangement is such that at least two support points will be created which will position the stool in a desired manner and non-rotatably in the examination opening (4). Preferably the positioning means (32, 33, 34) of the stool are also implemented such that they enable mutual relative movement of the O-arm (2) and the patient stool (30) essentially in the direction of the central axis of the structure (2) supporting the imaging means, which makes it possible to flexibly adjust height position of the field of view (FOV) with respect to the stool, and thus to the patients leg, by just changing the height position of the O-arm (2). In one preferable embodiment of the invention the structure, the dimensions and the proportions of the legs of the stool (30) and of the connection arrangement are realized, in relation to the vertical range of movement of the O-arm (2) and in a mode in which the patient stool (30) has been attached to the imaging apparatus, such that the stool stands on the floor regardless of the height on which the O-arm (2) is driven within the limits this operation mode of the apparatus allows for.

Even though preferable embodiments of the invention make possible realizing the O-arm (2) as a compact structure, the dimensions of the O-arm (2) are still in practise of such order of magnitude that especially concerning shorter and/or older patients, it is not that they would just simply step over the O-arm (2) into the examination opening (4). The length of the step needed can be shortened by using a patient stool (30) according to instant invention, whereby one does not need to come down all the way to the floor level when stepping inside the O-arm (2). The length of the step needed can further be shortened by arranging another stool, or stairs, also outside the O-arm (2).

On the other hand, in case the aim is to image e.g. patient's ankle or some other of the lower anatomies of a lower extremity in a standing position, such imaging would not necessarily even be possible without using a patient stool (30) or some other stand. When the lowest level whereto an O-arm (2), turned at a horizontal position, can be driven is the same (or higher) than the level on which the patient stands, it is the dimensions of the O-arm and, that is, especially the way in which the imaging means (21, 22) are arranged inside the O-arm (2), which always define some minimum height below which no anatomy can become imaged. Thus, in the case of the imaging apparatus having been mounted on the floor, for example, there always is a minimum lower limit for the field of view (FOV) of the O-arm (2) turned at a horizontal position locating higher than the floor level, but by positioning the patient himself on a level higher than the floor level (i.e., on a stool, for example), one is able within the limits of that height to also get the lowest parts of the lower extremity positioned at the minimum height level of the field of view of the imaging apparatus, or above it.

Figure 4A:
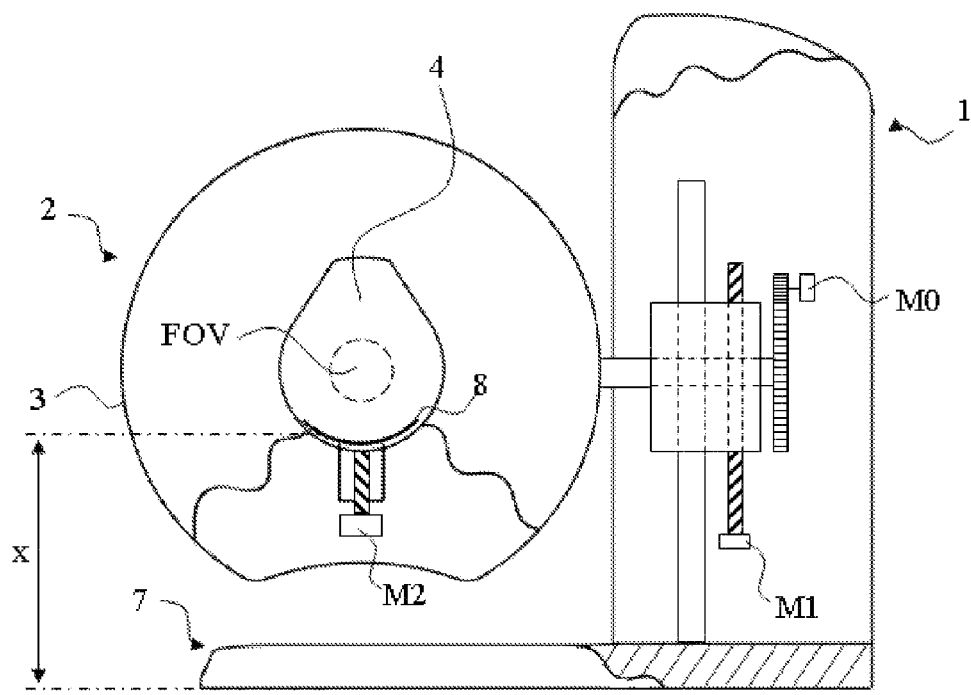
FIGS. 4a and 4b show one solution for moving a positioning support and the O-arm belonging to the apparatus.
Figure 4B:
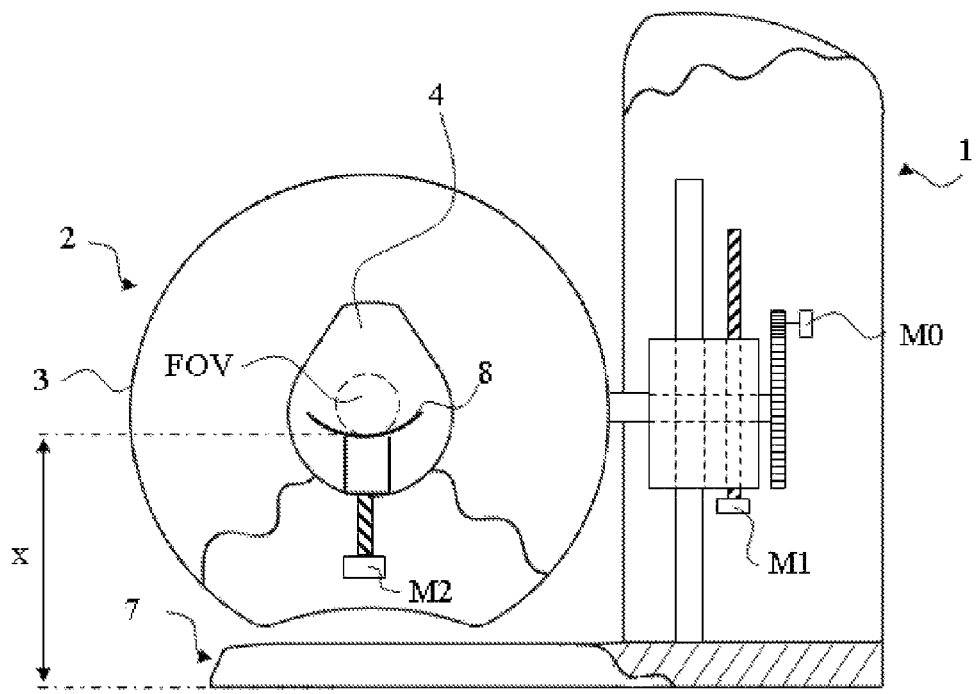

FIGS. 4a and 4b show one embodiment for motorized adjusting of the height position of the positioning support (8) being arranged to the apparatus (for adjusting location of the positioning support (8) with respect to the central axis of the O-arm (2)) and, besides, to function as synchronized with adjustment of the height position of the O-arm (2). Thus, considering imaging of a lower extremity at the seated position, for example, the positioning support (8) can be driven to its lowermost position with respect to the O-arm (2) with the help of the actuator (M0), and the O-arm (2) with the help of the actuator (M1) to such height position in which the positioning support (8) lying at its lowermost position will get positioned at the height level whereon one wishes it to lie during imaging. A positioning support (8) driven to its lowermost position leaves more room within the examination opening (4) for positioning an extremity and after one has managed to get the extremity positioned in a desired manner, the arrangement can be brought ready for imaging by driving the positioning support (8) upwards and the O-arm (2) downwards with an equal speed. This way, the positioning support (8) and thus also the patient's leg remain stationary with respect to "the set of coordinates of the patient" (distance x in the FIGS. 4a and 4b) while at the same time the area to become imaged—or rather the field of view (FOV)—moves to a desired place with respect to the anatomy one wishes to become imaged.

A corresponding functionality as discussed above can also be realized e.g. in connection with imaging a lower extremity in the standing position, i.e. whereupon the O-arm (2) is turned into a horizontal position. This embodiment of the invention has not separately been shown in the attached Figs. as the only new feature of the apparatus in this case is that the connection of the O-arm (2) to its support construction (1) is arranged to enable moving the O-arm (also) in the horizontal direction with respect to its support construction (1). Consequently, it is thus possible also in such imaging mode of the apparatus to drive, correspondingly as described above, the O-arm (2) and the positioning support (8) synchronized in opposite directions, i.e. in opposite horizontal directions while the patient stands in the examination opening (4) turned in horizontal orientation.

Figure 5A:
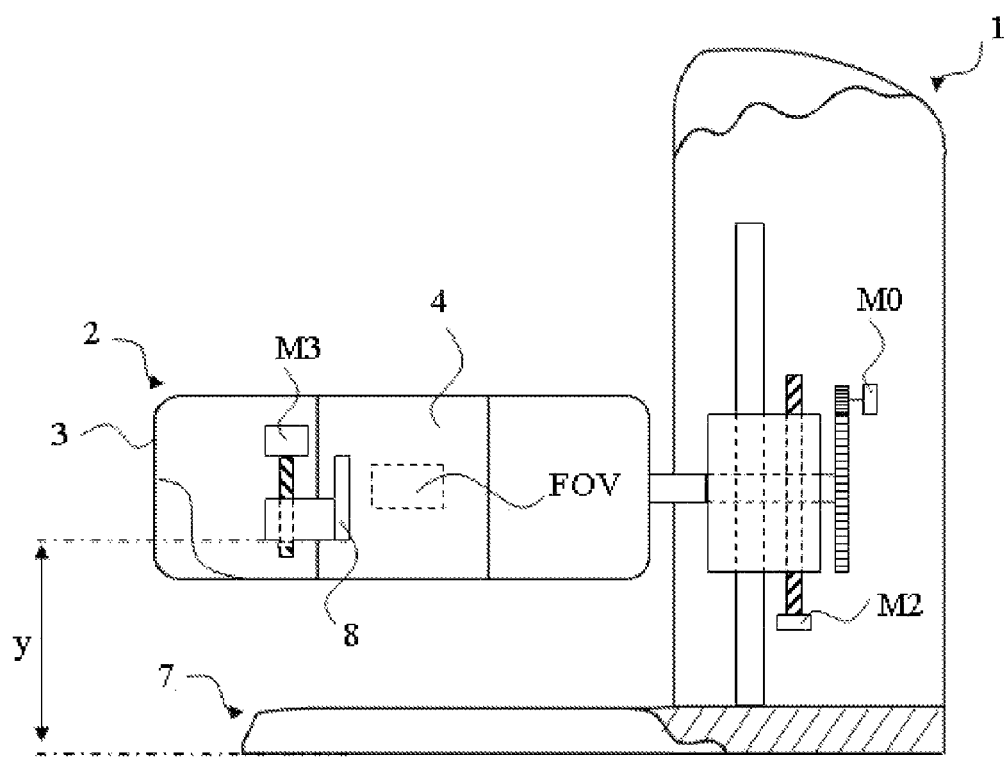
FIGS. 5a and 5b show another solution for moving the positioning support and the O-arm belonging to the apparatus.
Figure 5B:
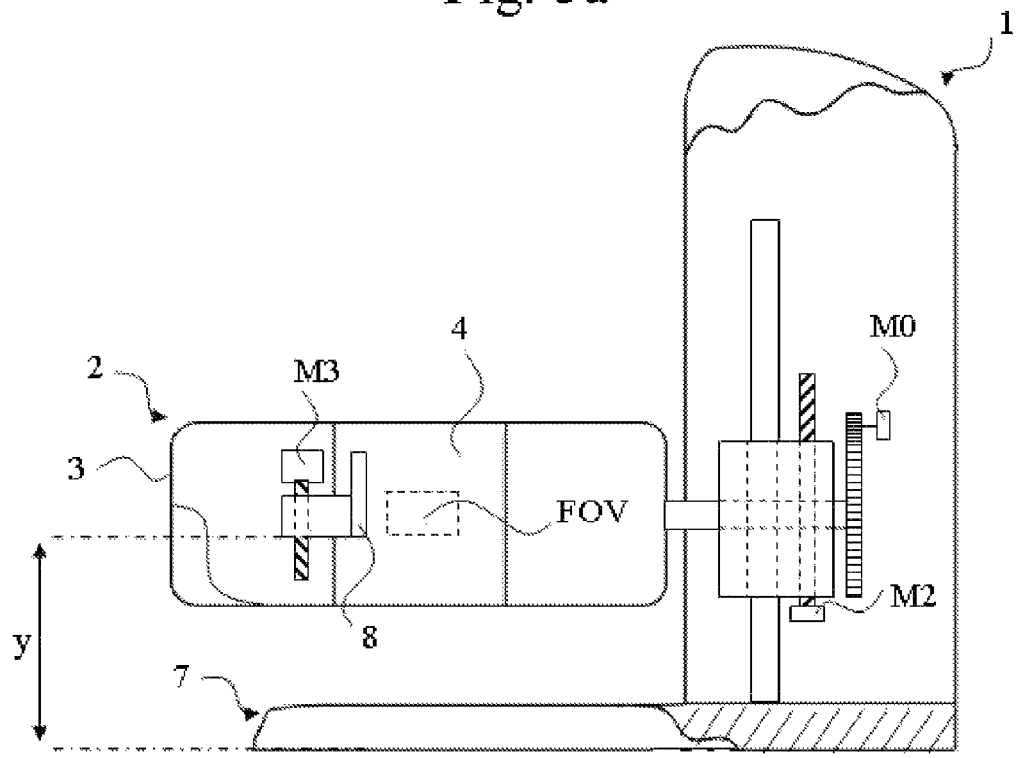

In FIGS. 5a and 5b yet another embodiment for adjusting location of the positioning support (8) with respect to location of the O-arm (2) is presented. In the solution according to these Figs. a freedom of movement parallel with the direction of the central axis of the O-arm (2) is arranged for the positioning support (8), which e.g. when imaging a lower extremity enables imaging of the leg from more than one place such that the patient needs not to be always repositioned for imaging. That is, it is then enough that the patient is positioned to the positioning support (8) once and thereafter, location of the field of view (FOV) with respect to the patient can be moved by a synchronized drive of the positioning support (8) and the O-arm (2) in opposite directions, whereby the positioning support (8) remains stationary with respect to the set of coordinates of the patient (cmp. distance y in FIGS. 5a and 5b).

A corresponding functionality as when driving the positioning support (8) by an actuator (M3) according to FIGS. 5a and 5b can also be realized by arranging the positioning support (8)—provided with a degree of freedom of movement parallel with the central axis of the O-arm (2)—to be attached to some structure which does not move along the movement of the O-arm (2) when it moves in the direction of its central axis. In principal, even the patient himself can be used as such a structure. So, as long as one stays within the area of movement arranged for the positioning support (8), by attaching the positioning support (8) e.g. by straps or tape to the patient's leg (or hand), it is possible to drive the O-arm (2) in the direction of its central axis (2) without the positioning support (8) moving along with the movement of the O-arm (2).

More generally speaking, thus, according to the invention a patient stool (4) is arranged in connection with the examination opening (4), preferably such that location of the stepping board (31) of the stool with respect to ring-shaped structure (2) is arranged adjustable. This adjusting is made possible by a construction which connects the patient stool (30) and the O-arm (2) together but such that when the O-arm (2) is moved in the direction of its central axis, within the operation range of said construction, the patient stool (30) remains stationary.

Above, an embodiment of the invention is disclosed in which a concave positioning support (8) or a patient stool (30) can alternatively be connected to the same connecting means arranged to the apparatus, the latter by means of a separate adapter or connecting piece (33), for example. However, the apparatus can also be realized such that the positioning support (8) and the patient stool (30) may be used at the same time. This can be realized e.g. by arranging the positioning support (8) and the stool (30) with connecting means of their own, by arranging the adapter (33) or the O-arm (2) itself with a connecting structure to which both the positioning support (8) and the stool (30) can be connected, or by providing an integrated positioning support—stool construction.

Considering the possible moving of the positioning support (8), a control function can be arranged in the control system of the apparatus for moving the positioning support (8) by at least one actuator in the first direction and at the first speed within the area of the examination opening of the substantially ring-shaped structure (2) which supports the imaging means, and for simultaneously moving the ring-shaped structure (2) supporting the imaging means with respect to said support construction (1) by at least one actuator substantially at said first speed substantially at opposite direction than said first direction. The movement of the positioning support (8) in the first direction can comprise moving of the positioning support (8) substantially in the direction perpendicular to the direction of the central axis of said ring-shaped structure (2) towards the central axis of the examination opening (2). Thus, according to different embodiments, when the structure (2) supporting the imaging means is at the vertical orientation, said movement of the positioning support (8) in the first direction can comprise moving the positioning support (8) in the vertical direction, whereupon said movement of the structure (2) supporting the imaging means in the opposite direction comprises vertical movement of the structure (2) supporting the imaging means with respect to its said support construction (1) and, corres-pondingly, when the structure (2) supporting the imaging means is at the horizontal orientation, said movement of the positioning support (8) in the first direction comprises moving the positioning support (8) in the horizontal direction, whereupon said movement of the structure (2) supporting the imaging means in the opposite direction comprises horizontal movement of the structure (2) supporting the imaging means with respect to its said support construction (1).

Considering imaging to be performed by the apparatus, the angle of rotation of the imaging means (21, 22) previously described above is sufficient in cone-beam tomography, in which the beam generated by the source of radiation (21) is arranged to be limited to a true two-dimensional beam and the receiver of image information (22), again, of its form and dimensions at least such that it covers said two-dimensional beam. In the apparatus according to the invention, such beam can also be arranged to be limited to more than one size and/or shape, whereby the receiver of image information (22) must naturally be arranged either to cover all possible beam sizes and shapes or it must be arranged changeable.

The projecting base part (7) arranged attachable into connection with the support construction (1) shown in FIG. 1 can be a component optionally arranged to the apparatus and its use is advantageous particularly when there is no intention to bolt or otherwise mount the support construction (1) on the floor, or if the location where the apparatus is considered to be used does not enable floor mounting. The projecting base part (7) assists the apparatus staying upright and, at the same time, it is e.g. possible to arrange wheels under the projecting base part (7) and the support construction (1) to facilitate transfer of the apparatus, such as transferring it from one imaging room to another. Considering these various possible ways to install the apparatus, it is preferable to arrange the projecting base part (7) detachably attachable to the support construction (1) of the apparatus.

In the embodiment according to FIG. 1, an opening (10) located substantially below the O-arm (2) has been arranged to the projecting base part (7). The purpose is that this opening (10) shall locate at a point where the patient stool (30) will get positioned when being set to its place in the examination opening (4) of the O-arm (2). This is one way to realize the patient stool (30) always becoming positioned at the same level with respect to the apparatus, regardless whether the apparatus is mounted with or without the base part, i.e. the stool (30) and its connecting mechanism can be identical regardless whether the base part (7) is used or not.

In the embodiment according to FIG. 1, the user interface of the apparatus is also in functional connection with the joy stick (9) arranged in connection with the O-arm (2). The ergonomic positioning of this joy stick (9) enables moving the O-arm (2) without the need for one to move away from the immediate proximity of the O-arm (2), and thus also from the patient. Preferably, the joy stick (9) is arranged to operate at least such that moving it downwards moves the O-arm (2) downwards and moving it upwards moves the O-arm (2) upwards.

The preferable embodiment of the invention shown in FIG. 1 can be implemented as a relatively compact structure and, for achieving many of the advantages described above, as a structure where the radius of the prevailing portion of the examination opening (4) being of the shape of an arch of a circle is of the order of 15 cm or slightly more and, on the other hand, the radius of the prevailing portion of the O-arm (2) of the shape of an arch of a circle is of the order of 50 cm or even less. Here, the distance of the focus of the source of radiation (21) from the centre of rotation of the imaging means (21, 22) can preferably be arranged e.g. for about 390 mm and that of the receiver of image information for about 190 mm.

It is obvious for one skilled in the art that as for its details, the present invention may be implemented also in other ways than according to the embodiments of the invention described above.

The invention claimed is:

1. A medical x-ray imaging apparatus, which apparatus includes
a support construction which is arranged to support a substantially ring-shaped structure supporting imaging means, which imaging means include a source of radiation and a receiver of image information, which imaging means are arranged within said substantially ring-shaped structure supporting the imaging means substantially on opposite sides of each other and movable within said ring-shaped structure supporting the imaging means,
which apparatus includes in said ring-shaped structure supporting the imaging means an examination opening wherein the object to be imaged is positionable for imaging,
and in which apparatus said substantially ring-shaped structure supporting the imaging means is arranged movable with respect to said support construction at least in the vertical direction,
wherein a patient stool is arranged to be positioned in the examination opening and positioning means are arranged to position the patient stool in the examination opening, said positioning means selectively connecting the patient stool to the ring-shaped structure.

2. The imaging apparatus according to claim 1, characterized in that said positioning means include a means cooperating with the patient stool, which position the patient stool at a desired location with respect to the examination opening of the apparatus.

3. The imaging apparatus according to claim 1 characterized in that said positioning means include a means cooperating with the patient stool, which allow for a mutual respective movement between the structure supporting the imaging means and the patient stool substantially in the direction of the central axis of the structure supporting the imaging means.

4. The imaging apparatus according to claim 1, characterized in that said positioning means include a structure arranged in connection with either the patient stool or the examination opening and comprising at least one groove, profile or hole and, respectively, a corresponding cooperating guiding structure arranged in connection with either the examination opening or the patient stool comprising a guiding profile, a guiding rod or the like fitted to move in said groove, profile or hole.

5. The imaging apparatus according to claim 4, characterized in that the patient stool comprises a stepping board and said guiding rod or a corresponding structure is arranged below the stepping board of the patient stool and/or said structure comprising the groove or a corresponding structure is arranged detachably or non-detachably connected to said structure supporting imaging means.

6. The imaging apparatus according to claim 4, characterized in that said positioning means comprise at least two guiding rods and a slide structure cooperating with said guiding rods.

7. The imaging apparatus according to claim 1, characterized in that the patient stool is arranged detachably connected to the structure supporting imaging means by an arrangement via which at least one other accessory, such as a concave positioning support for an extremity, used for patient positioning can be arranged as detachably connected into connection with the examination opening, or at least one other accessory, such as a concave positioning support for an extremity, used for patient positioning is integrated with the patient stool, or said patient stool and positioning support are arranged simultaneously detachably connectable to the structure supporting imaging means.

8. The imaging apparatus according to claim 1, characterized in that said substantially ring-shaped structure supporting imaging means is arranged turnable with respect to an axis substantially parallel with a horizontal diagonal of a radial cross-section of said ring-shaped structure.

9. The imaging apparatus according to claim 1, characterized in that a means is arranged in the apparatus for recognizing the patient stool being connected to the apparatus and/or that the apparatus includes a control system arranged with an operation mode, which in the case of the patient stool being connected to the structure supporting the imaging means disables realization of at least one of movements dangerous in view of patient safety
- turning the structure supporting the imaging means,
- lifting the structure supporting the imaging means too high,
- lowering the structure supporting the imaging means too low.

10. The imaging apparatus according to claim 1, characterized in that the source of radiation and the receiver of image information are arranged movable within said substantially ring-shaped structure supporting the imaging means with respect to a center of rotation such that the source of radiation moves at a different distance from said center of rotation than the receiver of image information.

11. The imaging apparatus according to claim 1, characterized in that within said ring-shaped structure supporting the imaging means is arranged a substantially ring-shaped support part, said source of radiation and receiver of image information are attached to that support part and said support part is arranged rotatable within the structure supporting the imaging means.

12. The imaging apparatus according to claim 1, characterized in that said substantially ring-shaped structure supporting the imaging means includes an outer cover the cross-section of which in a direction perpendicular with respect to the central axis of said ring-shaped structure is for its prevailing portion arranged substantially of the shape of an arch of a circle but to comprise a cut, and within the sector covered by the cut the distance from the center of said arch of a circle to the edge of the outer cover is shorter than within said portion of the outer cover substantially of the shape of an arch of a circle, said extension of the examination opening is arranged to be located substantially on the opposite side of said ring-shaped structure supporting the imaging means than said cut of the outer cover, and a range of movement of said source of radiation within said ring-shaped structure supporting the imaging means is arranged not to extend to that sector of the structure supporting the imaging means wherein said cut of the outer cover has been made, and a range of movement of the receiver of image information is arranged not to extend to that sector of the structure supporting the imaging means wherein said extension of the examination opening has been arranged.

13. The imaging apparatus according to claim 12, characterized in that the receiver of image information is arranged to move closer to said center of rotation than the focus of said source of radiation, the outmost dimensions of said extension and cut from the center of rotation of the imaging means are arranged such that the source of radiation arranged to move farther from the center of rotation is able to move outside the extension of the examination opening and the receiver of image information inside the cut arranged to the outer cover of the structure supporting the imaging means.

14. The imaging apparatus according to claim 1, characterized in that the radius of the prevailing portion of said examination opening which is substantially of the shape of an arch of a circle is of the order of 15 cm or somewhat more, the radius of the prevailing portion of said structure supporting the imaging means which is substantially of the shape of an arch of a circle is of the order of 50 cm or less, and/or that the distance of the focus of the source of radiation from the center of rotation of the imaging means is about 390 mm and the distance of the receiver of image information from the center of rotation of the imaging means is about 190 mm.

15. The imaging apparatus according to claim 1, characterized in that a beam generated by said source of radiation is arranged to be limited to a true two-dimensional beam and, again, the receiver of image information for its form and dimensions at least such that it covers said two-dimensional beam.

* * * * *